United States Patent
Takakusagi et al.

(10) Patent No.: US 7,820,205 B2
(45) Date of Patent: Oct. 26, 2010

(54) PLATINUM COLLOID-CONTAINING AQUEOUS SOLUTION FOR TREATING SCHIZOPHRENIA

(75) Inventors: Mamoru Takakusagi, Iruma-gun (JP); Shigeki Shimizu, Machida (JP); Hirofumi Tsuji, Izu (JP)

(73) Assignee: Inovex Co., Ltd., Izu-Shi (JP)

( * ) Notice: Subject to any disclaimer, the term of this patent is extended or adjusted under 35 U.S.C. 154(b) by 786 days.

(21) Appl. No.: 11/664,692

(22) PCT Filed: Sep. 29, 2005

(86) PCT No.: PCT/JP2005/018008

§ 371 (c)(1),
(2), (4) Date: Apr. 5, 2007

(87) PCT Pub. No.: WO2006/038528

PCT Pub. Date: Apr. 13, 2006

(65) Prior Publication Data
US 2008/0031953 A1    Feb. 7, 2008

(30) Foreign Application Priority Data
Oct. 5, 2004  (JP) .............................. 2004-292543

(51) Int. Cl.
*A61K 33/24* (2006.01)
*A61K 9/14* (2006.01)
(52) U.S. Cl. ...................................... 424/649; 424/484
(58) Field of Classification Search ........................ None
See application file for complete search history.

(56) References Cited

U.S. PATENT DOCUMENTS
6,455,594 B1    9/2002    Tsuji et al.

FOREIGN PATENT DOCUMENTS

| JP | 4-141179 A | 5/1992 |
|---|---|---|
| JP | 2002-212102 A | 7/2002 |
| JP | 2005-270938 | 10/2005 |
| JP | 2006-337766 | 12/2006 |
| WO | 97/47291 A1 | 12/1997 |
| WO | 00/31120 A2 | 6/2000 |
| WO | 03/066071 A1 | 8/2003 |

OTHER PUBLICATIONS

Ryushi et al., "Physiological Effects of Negative Air Ions on the Recovery of Fatigue After Exercise," Japanese Journal Clinical Ecology, vol. 6, No. 1 (1997).

Yamada and Chino, "Inhibitory Effects of Negative Air Ions on Erythrocytes Aggregation," vol. 141, No. 3 (2000), Igaku To Seibutugaku.

Hyvert, M., " On the treatment of primary psychoses by the administration of gold salts," Annales Medico-Psychologiques, Fortin, Paris, FR, vol. 1, No. 5, Jan. 1, 1947, pp. 510-514, XP009124436, ISSN: 0003-4487.

European Search Report and Opinion, Reference GPS/FP6455588, Application No./Patent No. 05788190.6-2112/1803460, PCT/JP2005018008, Applicant—Inovex CO. LTD., dated Nov. 5, 2009, 6 pages.

*Primary Examiner*—Olga N Chernyshev
(74) *Attorney, Agent, or Firm*—Rothwell, Figg, Ernst & Manbeck pc

(57) ABSTRACT

The present invention provides a composition comprising precious metal particles for treating or preventing a psychiatric symptom. The composition of the invention is able to improve various psychiatric symptoms and useful for treating or preventing psychiatric disorders.

6 Claims, 3 Drawing Sheets

PLATINUM COLLOID-CONTAINING AQUEOUS SOLUTION FOR TREATING SCHIZOPHRENIA

CROSS-REFERENCE TO RELATED APPLICATION

The present application is a national stage filing under 35 U.S.C. §371 of PCT/JP2005/018008, filed on 29 Sep. 2005. The present application also claims priority under 35 U.S.C. §119 to Japanese patent application Serial No. 2004292543 filed on 5 Oct. 2004.

TECHNICAL FIELD

The present invention relates to a composition comprising precious metal particles for treating or preventing a psychiatric symptom. The present invention further relates to a method for treating or preventing a psychiatric symptom in a subject which comprises administering precious metal particles to the subject, and use of precious metal particles in the preparation of a composition for treating or preventing a psychiatric symptom.

BACKGROUND ART

In recent years, the prevalence rate of psychiatric disorders has increased due to the stress resulting from, for example, interpersonal relationship, economic problems, environmental destruction, and pollution problems. In certain psychiatric disorders, an excitement of dopaminergic nervous system is considered to be involved and therapeutic agents including antipsychotic agents have been used for the treatment. Antipsychotic agents currently used in clinical practice are classified roughly into two groups, typical antipsychotics and atypical antipsychotics. Typical antipsychotic agents exhibit their therapeutic effects through the inhibitory activity against the dopamine receptor, but also show side effects such as extrapyramidal symptom. Atypical antipsychotics, also called as SDAs (serotonin-dopamine antagonists), have the inhibitory activity on the serotonin receptor as well as the dopamine receptor and show fewer side effects than the typical antipsychotics. However, even atypical antipsychotics can not be completely free from side effects.

The effect of atmospheric ion on a living body has been attracting attention for many years. "Atmospheric ion" is a generic name of charged particles floating in the air. The atmospheric ion is classified into large ion and small ion, wherein the small ion has greater effects on a living body. The small ion is generated from disruption of water droplets which occurs around a waterfall and a stream in nature. Such phenomenon is called as waterfall effect (or Lenard's effect). The small ion is also produced by, for example, radiation of cosmic ray or from radioactive substances, electrolytic dissociation of atmospheric components occurring in lightning or corona discharge, or radiation from a radon hot spring. The small ion is a ultrafine particle being nanometer (nm)-order ($10^{-3}$ μm or less) and can be classified into positive air small ion (presumed chemical formula: $H_3O^+ \cdot (H_2O)_n$) and negative air small ion (presumed chemical formula: $O_2^- \cdot (H_2O)_n$). The negative air small ion is shown to significantly reduce the levels of dopamine and serotonin in blood which have been increased with physical exercise, during the recovery period from fatigue after the exercise (Non-patent literature 1). The negative air small ion is also considered to affect a living body by donating an electron ($e^-$) (Non-patent literature 2).

The negative air small ion is produced in nature and therefore it is not necessary to worry about the side effect on a living body. In order to benefit from the effect of the negative air small ion continuously, however, people have to live near a waterfall, or to always take a radon hot spring, which may restrict their living environment. Further, a negative air small ion generator utilizing water drop dissociation is not portable.

Non-patent literature 1: "Physiological effects of negative ions in the atmosphere on recovery from fatigue after exercise", Ryushi et al., Japanese Journal of Clinical Ecology, Vol. 6, No. 1 (1997)

Non-patent literature 2: "Effects of negative air ions to inhibit aggregation of erythrocytes", co-authored by Yamada and Chino, IGAKU TO SEIBUTUGAKU, Vol. 141, No. 3 (2000)

DISCLOSURE OF THE INVENTION

Problems to be Solved by the Invention

An object of the present invention is to provide a novel composition for treating or preventing symptoms involved in psychiatric disorders

Means to Solve the Problems

Japanese Patent Application Laid-open Nos. 2001-079382 and 2002-212102 by the present inventors disclose nanometer-sized precious metal particles. The present inventors have confirmed that a precious metal colloid-containing aqueous solution has a reduction ability, i.e. an electron donating property, by using a redox dye DCIP (2,6-dichloroindophenol sodium dihydrate) and a radical dye DPPH (1,1-diphenyl-2-picrylhydrazyl) (Japanese Patent Application No. 2004-092569) (the contents of the above references are incorporated herein by reference). Based on these findings, the inventors have administered the precious metal colloid-containing aqueous solution to patients of psychiatric disorders and observed improvements of various psychiatric symptoms, and thus have achieved the present invention.

The present invention provides:

(1) A composition comprising precious metal particles for treating or preventing a psychiatric symptom;

(2) The composition according to (1), wherein the average diameter of the precious metal particles is 2 to 5 nm;

(3) The composition according to (1) or (2), which is a precious metal colloid-containing aqueous solution;

(4) The composition according to (3), wherein the zeta potential of the precious metal colloid is −20 mV to −60 mV;

(5) The composition according to any one of (1) to (4), wherein the psychiatric symptom is selected from the group consisting of auditory hallucination, persecutory delusion, insomnia, anxiety, compulsion, apathy, screaming and self-injury;

(6) The composition according to any one of (1) to (5), which is used for treating or preventing schizophrenia;

(7) The composition according to any one of (1) to (6), wherein the precious metal is platinum;

(8) A method for treating or preventing a psychiatric symptom in a subject which comprises administering precious metal particles to the subject;

(9) The method according to (8), wherein the average diameter of the precious metal particles is 2 to 5 nm;

(10) The method according to (8) or (9), wherein a precious metal colloid-containing aqueous solution is administered;

(11) The method according to (10), wherein the zeta potential of the precious metal colloid is −20 mV to −60 mV;

(12) The method according to any one of (8) to (11), wherein the psychiatric symptom is selected from the group consisting of auditory hallucination, persecutory delusion, insomnia, anxiety, compulsion, apathy, screaming and self-injury;

(13) The method according to any one of (8) to (12), for treating or preventing schizophrenia;

(14) The method according to any one of (8) to (13), wherein the precious metal is platinum;

(15) Use of precious metal particles in the preparation of a composition for treating or preventing a psychiatric symptom;

(16) The use according to (15), wherein the average diameter of the precious metal particles is 2 to 5 nm;

(17) The use according to (15) or (16), wherein the composition is a precious metal colloid-containing aqueous solution;

(18) The use according to (17), wherein the zeta potential of the precious metal colloid is −20 mV to −60 mV;

(19) The use according to any one of (15) to (18), wherein the psychiatric symptom is selected from the group consisting of auditory hallucination, persecutory delusion, insomnia, anxiety, compulsion, apathy, screaming and self-injury;

(20) The use according to any one of (15) to (19), wherein the composition is used for treating or preventing schizophrenia;

(21) The use according to any one of (15) to (20), wherein the precious metal is platinum.

Effect of the Invention

The present invention is effective to improve various psychiatric symptoms and therefore is useful for treating or preventing psychiatric disorders with those psychiatric symptoms.

THE BEST MODE TO PRACTICE THE INVENTION

The present invention provides a composition comprising precious metal particles for treating or preventing a psychiatric symptom. The precious metal is, for example, platinum, palladium, gold or silver. Particularly, platinum, palladium and gold, which are approved as food additives, are preferred, and platinum and palladium are more preferred, and platinum is most preferred.

The precious metal particles are preferably nanometer-sized and more preferably have the average diameter of 2 to 20 nm, 2 to 10 nm or 2 to 5nm. The diameter of the precious metal particle may be determined by electron microscopic observation (TEM observation), for example, by using HF-2000 Cold Field Emission Transmission Electron Microscope (Hitachi, Ltd.) (Japanese Patent Application Laid-open No. 2002-212102, the reference is incorporated herein by reference).

The precious metal particles are preferred to be included in the composition of the invention as colloids. The composition of the invention is preferably a precious metal colloid-containing aqueous solution. "Precious metal colloid-containing aqueous solution" is an aqueous solution in which the precious metal particles are stably dispersed. The average diameter of the precious metal colloids is preferred to be 2 to 20 nm, 2 to 10 nm or 2 to 5 nm.

Figure 1:
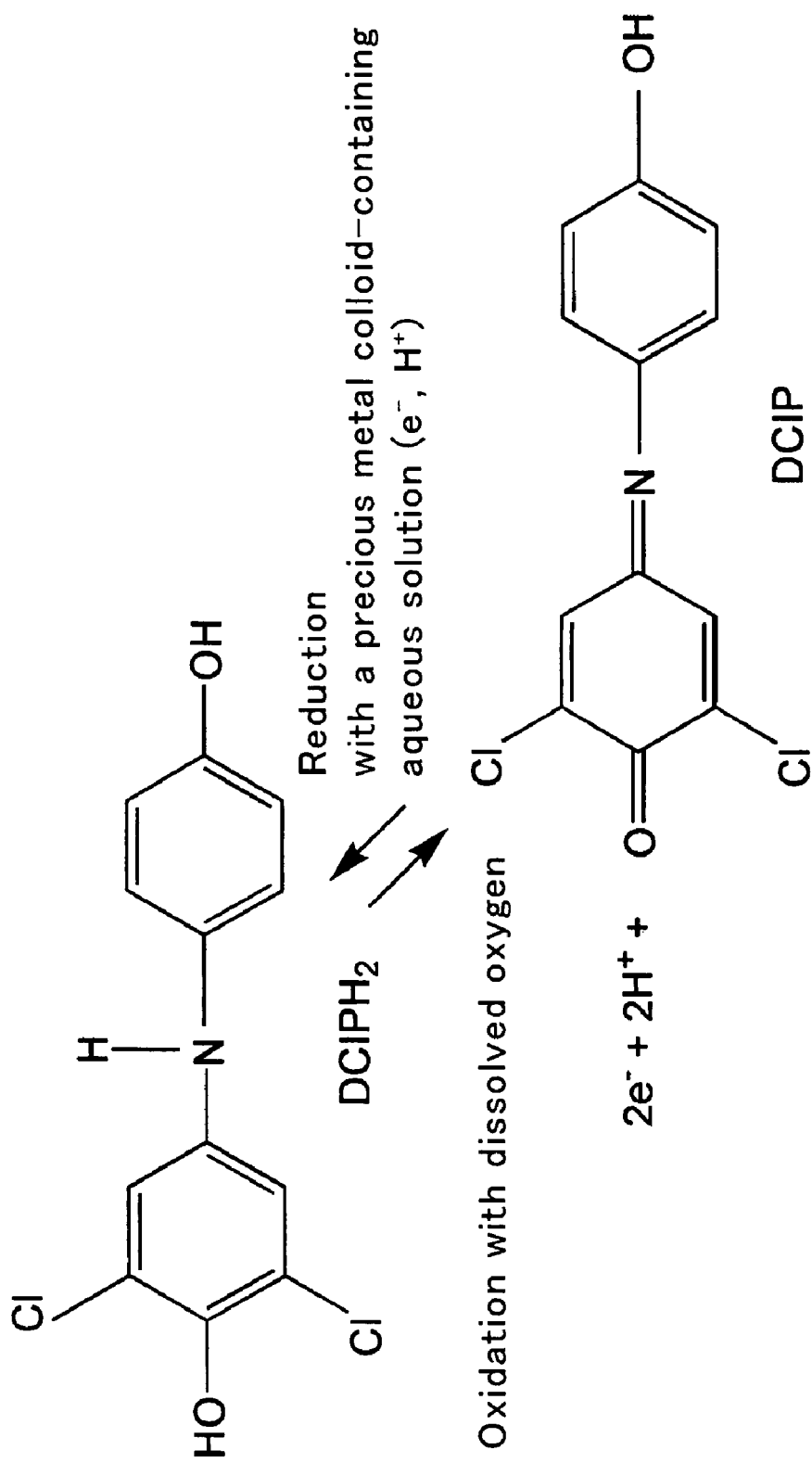
FIG. 1 shows a redox reaction of a redox dye, DCIP. DCIP (oxidized form) will be converted to $DCIPH_2$ (reduced form) upon donation of an electron ($e^-$) and proton ($H^+$).
Figure 2:
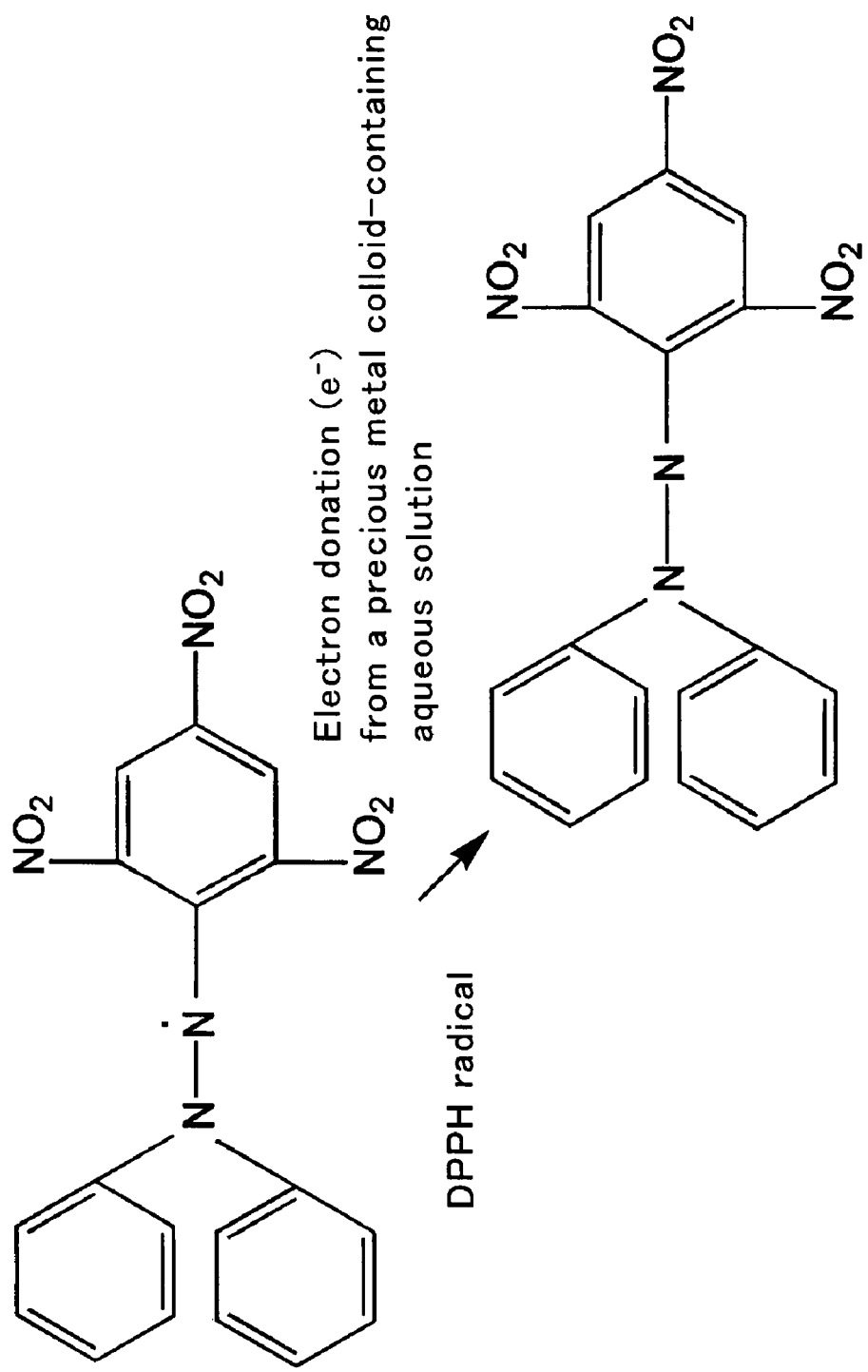
FIG. 2 shows a redox reaction of a radical dye, DPPH. When a DPPH radical receives an electron ($e^-$), the radical will disappear.
Figure 3:
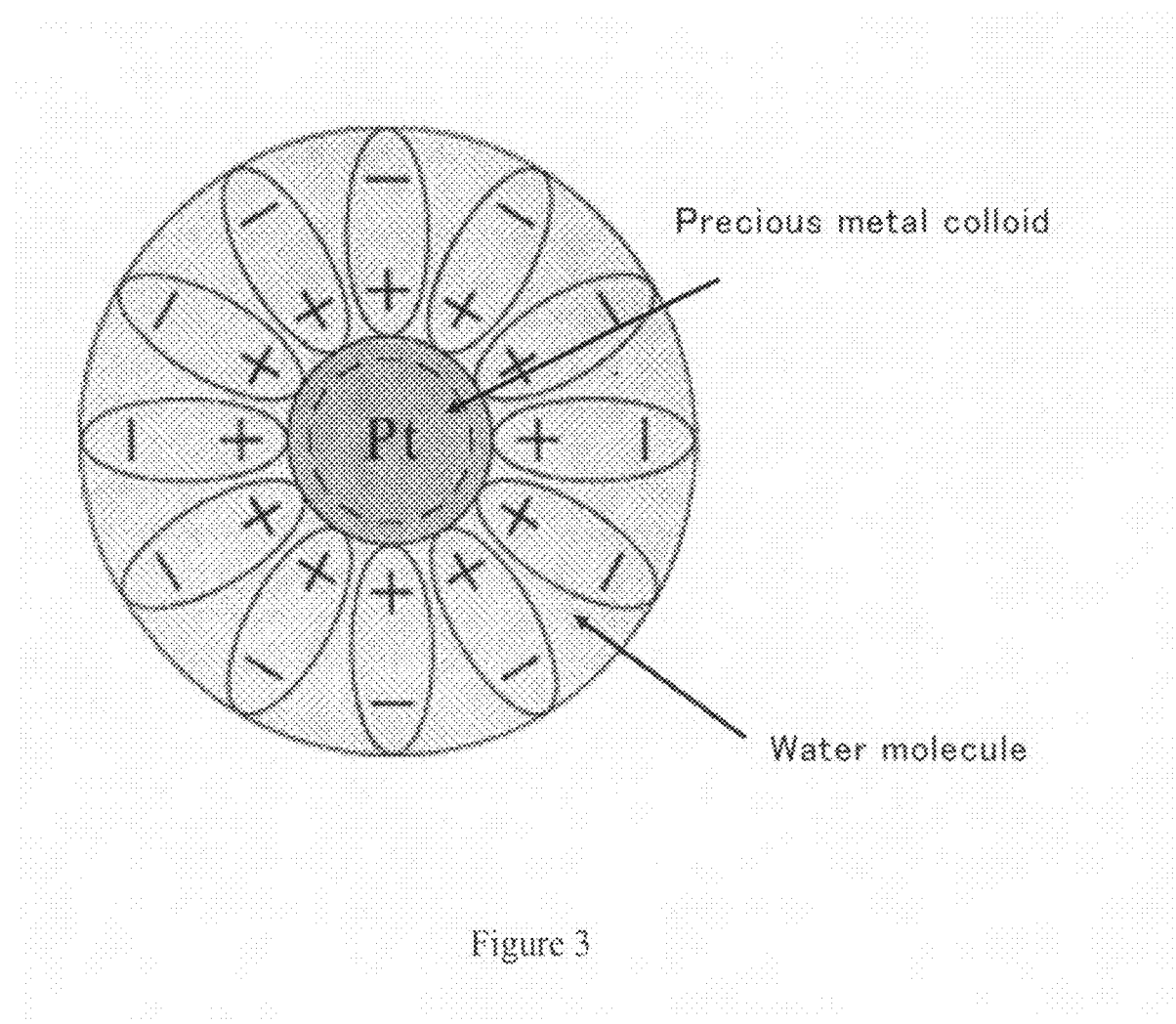
FIG. 3 is a diagram showing a precious metal colloid in a precious metal colloid-containing aqueous solution.

Water molecules around the precious metal colloid form a electric double layer by setting their positive ($H^+$) face to the precious metal particle while their negative ($OH^-$) face to its outer side due to the negative charge of the precious metal particle (FIG. 3). The charge of the precious metal colloid is expressed by zeta potential considering the electric double layer. The precious metal colloid of the invention preferably has the zeta-potential of −20 mV to −60 mV. The zeta-potential may be determined by an electrophoretic light scattering method (Japanese Patent Application Laid-open No. 2002-212102, the reference is incorporated herein by reference). Preferably, the precious metal colloid-containing aqueous solution used in the present invention contains substantially no electrolyte. "Containing substantially no electrolyte" used herein means that the concentration of electrolyte calculated on the assumption that the electrolyte is NaCl is less than 0.001 wt %.

The precious metal particle of the invention may be prepared by any method, and preferably by the metallic salt reduction method (Japanese Patent Application Laid-open No. 2001-079382, the reference is incorporated herein by reference). This method utilizes water, a precious metal ion solution, a reducing agent, a pH compensating agent and a surface-active substance.

The precious metal ion solution is an aqueous solution of a precious metal halide, for example, chloroplatinic acid, chloropalladic acid, chloroauric acid or silver nitrate. The precious metal ion solution is prepared by dissolving a commercially available precious metal halide in water.

The surface-active substance is added as a dispersion stabilizer to prevent precipitation and aggregation of the precious metal colloids. Although any known surface-active substance may be used, glycerin fatty acid esters, which can be used in food products, are preferred (Japanese Patent Application Laid-open No. 2005-163117, the reference is incorporated herein by reference). There are many types of glycerin fatty acid esters which vary in their HLB, polymerization degree of glycerin, type of fatty acid and degree of esterification. The glycerin fatty acid ester having HLB of equal to or more than 10 is suitable for the invention, and also the same having the polymerization degree of about 10 and the degree of esterification of 8 to 9% and whose fatty acid is lauric acid, stearic acid or oleic acid may be used. L-10D (Mitsubishi-Kagaku Foods Corporation), J-0381V (Riken Vitamin Co., Ltd.) and MSW-7S (SAKAMOTO INDUSTRY Co., Ltd) are commercially available glycerin fatty acid esters, for example. Sugars such as starch, which is edible, may also be used as a dispersion stabilizer. These dispersion stabilizers show less adverse effects on the digestive tract.

The reducing agent is added to reduce the precious metal ion. A low-molecular alcohol such as ethanol is a suitable reducing agent for the present invention, as a low-molecular alcohol shows less adverse effects on the digestive tract.

The pH compensating agent adjusts pH of the reaction solution, whose pH will be turned to be acidic upon addition of the precious metal ion solution, to neutral or weak alkaline. Therefore, the pH compensating agent is preferably added simultaneously with the precious metal ion solution. The pH compensating agent is preferably an alkaline metal compound, for example, sodium hydroxide, potassium hydroxide, sodium carbonate, potassium carbonate or sodium bicarbonate, with sodium bicarbonate being particularly preferred.

The procedure to prepare the precious metal colloid is illustrated, for example, as follows. First, the water is heated while being stirred to a predetermined temperature, and the surface-active substance or the dispersion stabilizer and the reducing agent are added to the heated water. Then, the precious metal ion solution and the pH compensating agent are added simultaneously to the solution. The reducing agent affects the precious metal ion to promote the reduction reaction of the precious metal ion in water. The solution is further stirred while being kept at a predetermined temperature, and the heating and stirring is stopped when the precious metal ion has been reduced. The reduction of the precious metal ion can be confirmed by the color change of the solution, i.e., the change to black in the case of platinum, palladium, silver and the like and to reddish purple in the case of gold. The temperature of the reduction process is 50 to 75° C. and desirably around 70° C. As a result of the reduction process, precious metal colloids are obtained in the reaction solution.

The concentration of the precious metal in the precious metal ion solution is not limited. The precious metal ion solution containing the precious metal ion at a one-fifth ratio in terms of weight (g)/volume (ml) ratio is illustrated by example, as described "chloroplatinic acid solution in water, 10 ml, (2 g Pt)" in the reference example. The amount of the water (ml) is 400 to 2,000 times of that of the precious metal ion solution which is represented as 1. The amount of the reducing agent and the pH compensating agent may be determined as appropriate depending on the type of the precious metal. When the amount of the water to be used is 400 to 2,000 times of that of the precious metal ion solution, 1, that of the reducing agent (ml) is 20 to 100 times (in the case of 99.5% alcohol) and that of the pH compensating agent (ml) is 10 to 30 times (in the case of 5 wt %), of that of the precious metal ion solution. The amount of the surface-active substance (g) is 1 to 10 times of that of the precious metal (g) in the precious metal ion solution. When the surface-active substance is glycerin fatty acid ester, the amount to be used (g) is 1 to 3, preferably 2, times of that of the precious metal (g) in the precious metal ion solution (Japanese patent application No. 2003-404273). Starch may be used in the amount similar to that of glycerin fatty acid ester.

The stability of the precious metal colloids produced is ensured by controlling the amount of the surface-active substance or the dispersion stabilizer as 1 to 10 times of the amount of the precious metal in the precious metal ion solution. When the amount of the water is greater in relation to that of the precious metal ion solution, the relative concentrations of the precious metal ion, the reducing agent, and the pH compensating agent are decreased, and the dispersion stability of the precious metal colloids produced will be adversely affected. In addition, when the concentration of the precious metal in the reduction process exceeds 2,000 ppm, the dispersion stability will be deteriorated.

In the following reference example, the reducing agent and the surface-active substance were added to the water to generate a reductive atmosphere in the solution first, and then, the precious metal ion solution was added to the solution. Alternatively, the reducing agent may be added after the addition of the precious metal ion solution and the pH compensating agent to the solution, wherein the water was added with the surface-active substance first while being heated.

After the above reduction process, a washing and purification process by filtration is performed for preventing contamination of, for example, dust, removing low-molecular ions other than the precious metal colloids, and desalting the solution. The desalting process may be performed by a conventional method, for example by dialysis using an ultrafilter membrane. The washing and purification process is completed when it is confirmed that no salt is detected in the permeated solution. The particle diameter of the precious metal colloid is ensured by the selection of the pore diameters of the filter and the ultrafilter membrane. Although the concentration of the precious metal in the precious metal colloid-containing aqueous solution may be adjusted as appropriate during this process, it is preferred to be adjusted by setting the ultrafiltration equipment at the concentration in the range of 200 to 2000 ppm, considering economical efficiency. Any concentration in the range of 95 to 102 wt % of the concentration being set is considered to be acceptable, and therefore, when the concentration is set at 200 ppm, 500 ppm or 2,000 ppm, the precious metal colloid-containing aqueous solution of 190 to 204 ppm, 475 to 510 ppm or 1,900 to 2,040 ppm will be obtained, respectively.

In addition to the precious metal particles, the composition of the invention may further comprise any appropriate solvent and/or additive and the like. The precious metal colloid-containing aqueous solution prepared by the above method is preferred as the composition of the invention.

The composition of the invention may be used for treating or preventing a psychiatric symptom. The term "psychiatric symptom" in the present specification and claims means various symptoms relating to psychiatric disorders, including auditory hallucination, persecutory delusion, insomnia, anxiety, compulsion, apathy, screaming and self-injury. The meaning of the treatment or prevention of a psychiatric symptom encompasses improvement of the symptom, inhibition of progression, prevention of development and reoccurrence.

The composition of the invention is useful for treating or preventing a psychiatric symptom, and thus may be used for treating or preventing any psychiatric disorder accompanied by the psychiatric symptom. It should be understood that the composition of the invention can be administered to a patient diagnosed as having a psychiatric disorder, as well as a patient who has not been diagnosed as having a psychiatric disorder but reports the psychiatric symptom mentioned above. The composition of the invention may be used not only as a pharmaceutical product but also as a health food product or a quasi drug.

The dosage of the composition of the invention is not limited, and may be selected as appropriate according to the age, body weight, condition and the like of the subject. For example, the precious metal colloid-containing aqueous solution of 500 ppm can be administered at a dosage of 1 to 500 ml per day, and also 4 to 200, 8 to 100, 10 to 30, or 15 to 20 ml per day. The composition of the invention may be diluted with water or other beverages, such as tea, coffee or juice before administration.

Although the present invention is further illustrated by the following reference examples and examples, it should not be limited in any sense by those examples.

EXAMPLE

Reference Example 1

Preparation of a Platinum Colloid-Containing Aqueous Solution (1)

A platinum colloid-containing aqueous solution was prepared using the following reagents. To prepare the water, purified water was filtered through the quantitative filter paper No. 5C, pore diameter 1 μm, Advantec Toyo Kaisha, Ltd.

TABLE 1

| Water | | 4300 ml |
|---|---|---|
| Reducing agent | Ethanol (99.5%) | 430 ml |
| Surface-active substance | Glycerin fatty acid ester (the followings were dissolved in water and mixed) L-10D 1 g/50 ml (Mitsubishi Kagaku Foods Corporation) J-0381V 3 g/50 ml (Riken Vitamin Co., Ltd.) | 4 g (100 ml) |
| Precious metal ion solution | Chloroplatinic acid solution in water | 10 ml (2 g Pt) |
| pH compensating agent | Sodium bicarbonate solution in water 10 g/200 ml, 5 wt % | 200 ml |

The water was poured into a vessel and heated while being stirred. When the temperature of the water reached to 60° C., the reducing agent and the surface-active substance were added. The mixture was heated further with stirring, and the precious metal ion solution and the pH compensating agent were added thereto when the temperature reached to 70° C. The reduction reaction was performed at 70° C. with stirring. The heating and stirring were stopped when the platinum ion was reduced to form platinum colloids (when the color of the solution turned to be black), and thus the reduction reaction was completed.

The resulting solution was filtered through a filter paper (quantitative filter paper No. 5C, pore diameter 1 μm, Advantec Toyo Kaisha, Ltd.). The filtrate was left to stand for 12 hours, and then concentration, as well as washing and purification, were performed using an ultrafilter membrane (10,000 molecular weight cut off, Nihon Millipore, Inc.), while being added with 15,000 ml of water. The concentration of the platinum was adjusted by setting the ultrafiltration equipment at 500 ppm. The salt content in the permeated solution was measured and the washing and purification process was completed at the time no salt was detected.

The diameter of the platinum colloids was measured with HF-2000 Cold Field Emission Transmission Electron Microscope (Hitachi, Ltd.) and shown to be 2 to 3 nm. The zeta potential of the platinum colloid was −42.1 mV, which was measured with an electrophoretic light scattering device (OT-SUKA ELECTRONICS CO., LTD.). The similar result was obtained as to a platinum colloid-containing aqueous solution which was prepared by setting the platinum concentration at 200 or 2,000 ppm.

Reference Example 2

Preparation of a Platinum Colloid-Containing Aqueous Solution (2)

A platinum colloid-containing aqueous solution was prepared using the following reagents in a similar way to the reference example 1.

TABLE 2

| Water | | 4500 ml |
|---|---|---|
| Reducing agent | Ethanol (99.5%) | 500 ml |
| Surface-active substance | Polysorbate 80 (Tween-80, KANTO CHEMICAL CO LTD.) | 5 ml |

TABLE 2-continued

| Precious metal ion solution | Chloroplatinic acid solution in water | 10 ml (2 g Pt) |
|---|---|---|
| pH compensating agent | Sodium bicarbonate solution in water 10 mg/100 ml, 10 wt % | 100 ml |

The concentration of platinum of the resulting aqueous solution was 510 ppm. The diameter of the platinum colloids measured with HF-2000 Cold Field Emission Transmission Electron Microscope (Hitachi, Ltd.) was 2 to 3 nm. The zeta potential measured with an electrophoretic light scattering device (OTSUKA ELECTRONICS CO., LTD.) was −41.2 mV.

Although preparation of a platinum colloid-containing aqueous solution was explained as above, precious metal-containing aqueous solutions which contain other precious metal colloids also could be prepared in the same manner, by using chloroauric acid solution, chloropalladic acid solution and the like as the precious metal ion solution.

Example

Improvement of Psychiatric Symptoms

The platinum colloid-containing aqueous solution prepared according to Reference Example 1 was sterilized by heat at 80° C. for 30 minutes and used for the test. The platinum colloid-containing aqueous solution (20 ml in Cases 1 to 3 and 10 or 15 ml in Cases 4 to 6 per day) was diluted with a commercially available mineral water to 500 ml, and 30 to 32 ml of the diluted solution was taken every hour from 6 a.m. to 10 p.m.

Case 1

A Patient of Schizophrenia, 29 Years-Old, Male

Clinical History and Course of the Disease

The patient developed the disease at the age of 11 and had suffered from auditory hallucination.

Drinking of the platinum colloid-containing aqueous solution was started without concomitant medication. Two weeks from the beginning of the drinking, the auditory hallucination disappeared for 2 hours. The patient still recognizes the efficacy.

Case 2

A Patient of Schizophrenia, 15 Years-Old, Female

Clinical History and Course of the Disease

The patient developed the disease at the age of 11 and had suffered from auditory hallucination and persecutory delusion. It caused school refusal and withdrawal.

Drinking of the platinum colloid-containing aqueous solution was started without concomitant medication. About 2 months later, it was reported that the persecutory delusion was slightly improved. Another month later, it was reported that the auditory hallucination was also reduced. Then, the patient began to go to school. Although she sometimes refused to go to school, she was leading a normal life by continuously drinking the platinum colloid-containing aqueous solution in the same manner, and the symptoms were diagnosed as being improved.

Case 3

A Patient of Schizophrenia, 32 Years-Old, Female

Clinical History and Course of the Disease

The patient developed the disease at the age of 24 and had suffered from psychiatric symptoms such as auditory hallucination, persecutory delusion, screaming and self-injury. She believed that resentment against her father led to the onset of the disease.

Drinking of the platinum colloid-containing aqueous solution was started with Risperdal (2 mg, twice a day in the morning and evening) and Seroquel (25 mg, 3 tablets a day in the evening). Serenace (5 mg a day in the evening) which had been used was withdrawn. About a month later, the screaming was reduced, and the persecutory delusion and the auditory hallucination were started to be improved. Another two months later, the self-injury was almost disappeared. Six months from the beginning of the treatment, she could talk cheerfully with her family and the relationship with her father was improved, and she could lead a normal life. Further, it was reported that she became healthy, cheerful, and positive, and the symptoms were diagnosed as being improved.

Case 4

A Patient of Schizophrenia, 40 Years-Old, Male

Clinical History and Course of the Disease

The patient developed insomnia, delusion, auditory hallucination and ophthalmophobia at the age of 21. He was under the delusion that a bugging device was placed, people talked about him behind his back, he was derided, and the like. He had received psychiatric treatment for 3 years and after that, stopped taking the therapeutic agents on his own since improvement of the symptoms was observed, which resulted in a recurrence of the disease. The symptoms got worse than before, and the predominant symptoms were insomnia, auditory hallucination and persecutory delusion. There was no improvement observed in spite of restarting psychiatric treatment, and he was put into a group home. He continuously experienced insomnia, auditory hallucination of derision and persecutory delusion, and was basically stay-at-home and did not go to the group home more than once a week.

From Sep. 1, 2004 (at the age of 39), drinking of the platinum colloid-containing aqueous solution was started in combination with the psychotropic agents which had been used. With the drinking of the platinum colloid-containing aqueous solution, his sleeping time increased from 4 to 5 hours to 8 hours. Although the sleeping time varied, his physical condition was getting better and the strong anxiety during the daytime and a part of the persecutory delusion were disappeared. He still had his specific gynephobia, but could go to a coffee shop and even make a short trip. The insomnia, anxiety and persecutory delusion were diagnosed as being significantly improved. Improvement of the auditory hallucination is now being monitored.

Case 5

A patient of Schizophrenia, 21 Years-Old, Female

Clinical History and Course of the Disease

The patient developed the disease at the age of 13. The predominant symptom was persecutory delusion, because of which she feared all people around her including her friends and refused to go to school, resulting in withdrawal. She always had anxiety, which was suddenly enhanced. At the age of 16, she developed confusion and became to talk nonsense words. She had no memory and was promptly hospitalized for, 3 months. After that, she was voluntarily hospitalized again because of her sudden anxiety. Although she had been administered with psychotropic agents since January 2004 (at the age of 20), she stopped taking the agents on her own and was stay-at-home due to the continuous anxiety and persecutory delusion.

From Sep. 5, 2004, drinking of the platinum colloid-containing aqueous solution was started. She reported that the anxiety and persecutory delusion were disappeared, which allowed her to go out. The anxiety and persecutory delusion were diagnosed as being significantly improved.

Case 6

A Patient of Schizophrenia, 30 Years-Old, Male

Clinical History and Course of the Disease

The patient started to feel anxiety and impatience from the spring at the age of 18, because he felt his classes difficult after entering university. His clothes and lifestyle became demoralized and he sometimes missed school, but he attended ordinarily during the first semester. However, the symptoms gradually got to be worse, and he lost his energy and started to feel that someone talked about him outside a window. Because of this, he became to stay at his room so log time and sometimes screamed. Although he saw a doctor of the neighborhood and was administered with psychotropic agents in this period, the symptoms got to be worse. He took off school after a year and went back to his hometown. Due to the medication from a doctor at his hometown, the symptoms were relatively calmed down although they occasionally varied. Even so, he sometimes felt that he could see a fox in a mirror, there was someone on the ceiling, his entity was exchanged with that of another person, and something like an insect was creeping in his body. Further, he felt his farther was duty, and therefore he had to wash his hands many times when he touched something his farther had touched before. He did not go out and stayed at home almost all the time with apathy. He made a suicide attempt twice during that period.

Drinking of the platinum colloid-containing aqueous solution, 10 ml per day in a manner described above, was started from May 17, 2004 (at the age of 29). At the onset, the predominant symptoms were compulsive neurosis and withdrawal from apathy, and hallucination and apparent persecutory delusion were not observed. The dosage was increased to 15 ml per day from June 28 of the same year since no improvement was observed. Five months later, he could go out for a while. Then, the frequency of hand-washing decreased to 50 to 60% than before. Subsequently, he became not reluctant to go out, and the symptoms were diagnosed as being significantly improved. Drug-induced hepatitis of the patient was not worsened by the drinking of the platinum colloid-containing aqueous solution.

The invention claimed is:

1. A method for treating schizophrenia in a subject which comprises orally administering a platinum colloid-containing aqueous solution to the subject.

2. The method according to claim 1, wherein the schizophrenia is accompanied by a psychiatric symptom selected from the group consisting of auditory hallucination, persecutory delusion, insomnia, anxiety, compulsion, apathy, screaming and self-injury.

3. The method according to claim 1, wherein the platinum colloid-containing aqueous solution is administered at a dosage corresponding to 1 to 500, 4 to 200, 8 to 100, 10 to 30 or 15 to 20 ml per day of a platinum colloid-containing aqueous solution of 500 ppm.

4. The method according to claim 1, wherein the zeta potential of the platinum colloid is −20 mV to −60 mV.

5. The method according to claim 1, wherein the average diameter of the platinum particles in the platinum colloid-containing aqueous solution is 2 to 5 nm.

6. The method according to claim 5, wherein the zeta potential of the platinum colloid is −20 mV to −60 mV.

* * * * *